US00PP13584P2

(12) United States Plant Patent
Kolster

(10) Patent No.: US PP13,584 P2
(45) Date of Patent: Feb. 18, 2003

(54) PHOTINIA PLANT NAMED 'KOLCURL'

(75) Inventor: Peter R. Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/006,812

(22) Filed: Dec. 5, 2001

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Photinia plant named 'Kolcurl' characterized by its upright and outwardly spreading plant habit; dark reddish brown stem coloration; leaves that are brown when developing and green when fully expanded; and undulating leaves with serrulate margins.

2 Drawing Sheets

BOTANICAL CLASSIFICATION/CULTIVAR DESIGNATION

*Photinia serrulata* cultivar Kolcurl.

BACKGROUND OF THE INVENTION

The present Invention relates to a new and distinct cultivar of Photinia plant, botanically known as *Photinia serrulata*, and hereinafter referred to by the name 'Kolcurl'.

The new Photinia is a product of a planned breeding program conducted by the Inventor in Wageningen, The Netherlands. The objective of the breeding program was to develop new Photinia cultivars with attractive leaves.

The new cultivar originated from a cross made by the Inventor in 1990 of two unidentified proprietary seedling selections, not patented. The cultivar Kolcurl was discovered and selected by the Inventor in 1995 as a single plant within the progeny of the stated cross in a controlled environment in Wageningen, The Netherlands.

Asexual reproduction of the new Photinia by terminal cuttings taken at Boskoop, The Netherlands, has shown that the unique features of this new Photinia are stable and reproduced true to type in successive generations of asexual reproduction.

SUMMARY OF THE INVENTION

The following traits have been repeatedly observed and are determined to be the unique characteristics of 'Kolcurl'. These characteristics in combination distinguish 'Kolcurl' as a new and distinct cultivar:

1. Upright and outwardly spreading plant habit.

2. Dark reddish brown stem coloration.

3. Leaves that are brown when developing and green when fully expanded.

4. Undulating leaves with serrulate margins.

Plants of the new Photinia differ from plants of the parent seedling selections primarily in leaf characteristics as plants of the parent selection do not have undulating leaves.

Plants of the new Photinia can be compared to plants of the Photinia cultivar Red Robin, not patented. In side-by-side comparisons conducted in Boskoop, The Netherlands, plants of the new Photinia differed from plants of the cultivar Red Robin in the following characteristics:

1. Plants of the new Photinia had undulating leaves whereas plants of the cultivar Red Robin had smooth, non-undulating leaves.

2. Plants of the new Photinia grew continuously whereas plants of the cultivar Red Robin grew intermittently.

3. Plants of the new Photinia were more resistant to pathogens and pests than plants of the cultivar Red Robin.

BRIEF DESCRIPTION OF THE PHOTOGRAPHS

The accompanying colored photographs illustrate the overall appearance of the new Photinia, showing the colors as true as it is reasonably possible to obtain in colored reproductions of this type. Colors in the photographs may differ slightly from the color values cited in the detailed botanical description which accurately describe the colors of the new Photinia.

The photograph on the first sheet comprises a side perspective view of a typical plant of 'Kolcurl'.

The photograph at the top of the second sheet is a close-up view of a typical upper surface of a developing leaf of 'Kolcurl'.

The photograph at the bottom of the second sheet is a close-up view of a typical upper surface of a fully expanded leaf of 'Kolcurl'.

DETAILED BOTANICAL DESCRIPTION

The new Photinia has not been observed under all possible environmental conditions. The phenotype may vary somewhat with variations in environment such as temperature and light intensity, without, however, any variance in genotype.

The aforementioned photographs, following observations and measurements describe plants grown in Boskoop, The Netherlands, in an outdoor nursery and under commercial production practices. Plants were about three years old and pruned annually. The photographs and description were taken during the summer when day temperatures ranged from 14 to 20° C and night temperatures ranged from 7 to 12° C.

In the following description, color references are made to The Royal Horticultural Society Colour Chart, 2001 Edition, except where general terms of ordinary dictionary significance are used.

Botanical classification: *Photinia serrulata* cultivar Kolcurl.

Parentage:

*Female parent*.—Unidentified proprietary selection of *Photinia serrulata*, not patented.

*Male parent*.—Unidentified proprietary selection of *Photinia serrulata*, not patented.

Propagation:

*Type*.—Terminal cuttings.

*Time to initiate roots*.—About 30 days at 20° C.

*Time to produce a rooted young plant*.—About 90 days at 20° C.

*Root description*.—Medium thickness; dark brown in color.

Plant description:

*Plant form*.—Upright and outwardly spreading perennial evergreen shrub.

*Growth habit*.—Moderately vigorous. Dense and bushy growth habit.

*Plant height*.—1.5 m.

*Plant width* (*spread*).—About 1.5 m.

*Growth rate*.—Plants grow about 20 cm per month during the spring in Boskoop, The Netherlands.

*Lateral branches*.—Quantity per plant: About 9. Length: About 70 cm. Diameter: About 4 mm. Internode length: About 2.4 cm. Strength: Strong. Texture: Smooth. Color: 183A to 183B.

*Foliage description*.—Leaves alternate, single, and generally symmetrical. Quantity per lateral branch: About 29. Length: About 11.8 cm. Width: About 6.1 cm. Shape: Obovate. Apex: Abruptly acute to mucronulate. Base: Attenuate. Margin: Serrulate; undulate. Texture: Glabrous; leathery. Venation pattern: Pinnate. Color: Developing leaves, upper surface: Initially 172A, becoming more brown, between 166B and N199C, with subsequent development. Developing leaves, lower surface: Initially 182B to 182C, becoming more brown, lighter than 177D, with subsequent development. Fully expanded leaves, upper surface: More green than 137A. Fully expanded leaves, lower surface: 143C to 144B. Venation, upper surface: 143B to 143C. Venation, lower surface: 144A. Petiole: Length: About 1.1 cm. Diameter: About 3 mm. Color, upper and lower surfaces: 144A overlain with anthocyanin, 183A to 183B. Stipules: Quantity per leaf: Two. Arrangement/appearance: One stipule on either side of the base of the petiole; scale-like. Shape: Lanceolate. Apex: Acuminate. Length: About 5 mm. Width: About 2 mm. Color: Upper surface: 185A. Lower surface: 144B, overlaid with anthocyanin, 185A.

Flower description: Flowers have not been observed.

Disease/pest resistance: In comparison to other known Photinia cultivars, plants of the new Photinia have been observed to be relatively more resistant to pathogens and pests common to Photinia.

Temperature tolerance: Plants of the new Photinia have been observed to tolerate temperatures ranging from −15 to 35° C.

It is claimed:

1. A new and distinct cultivar of Photinia plant named 'Kolcurl', as illustrated and described.

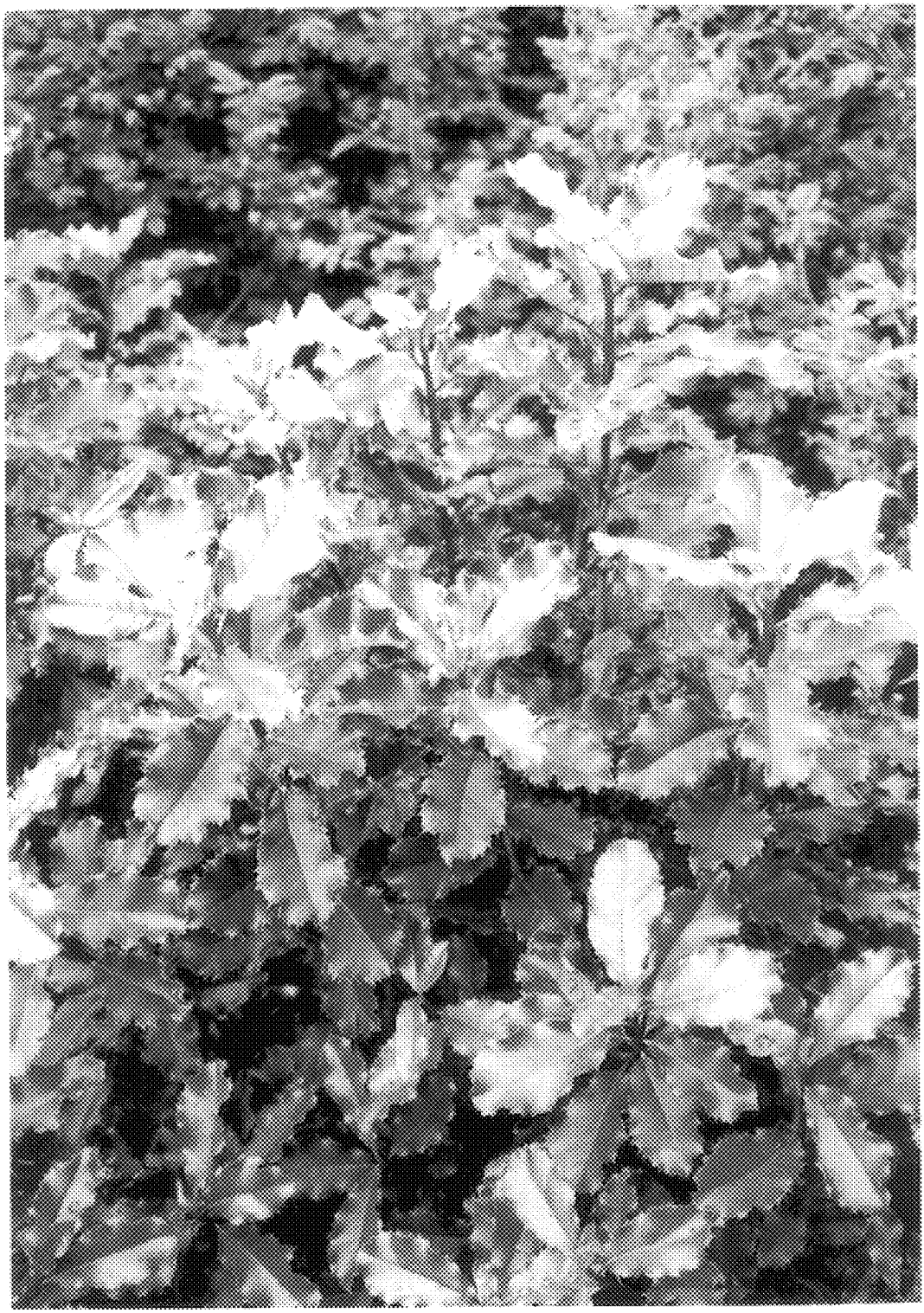

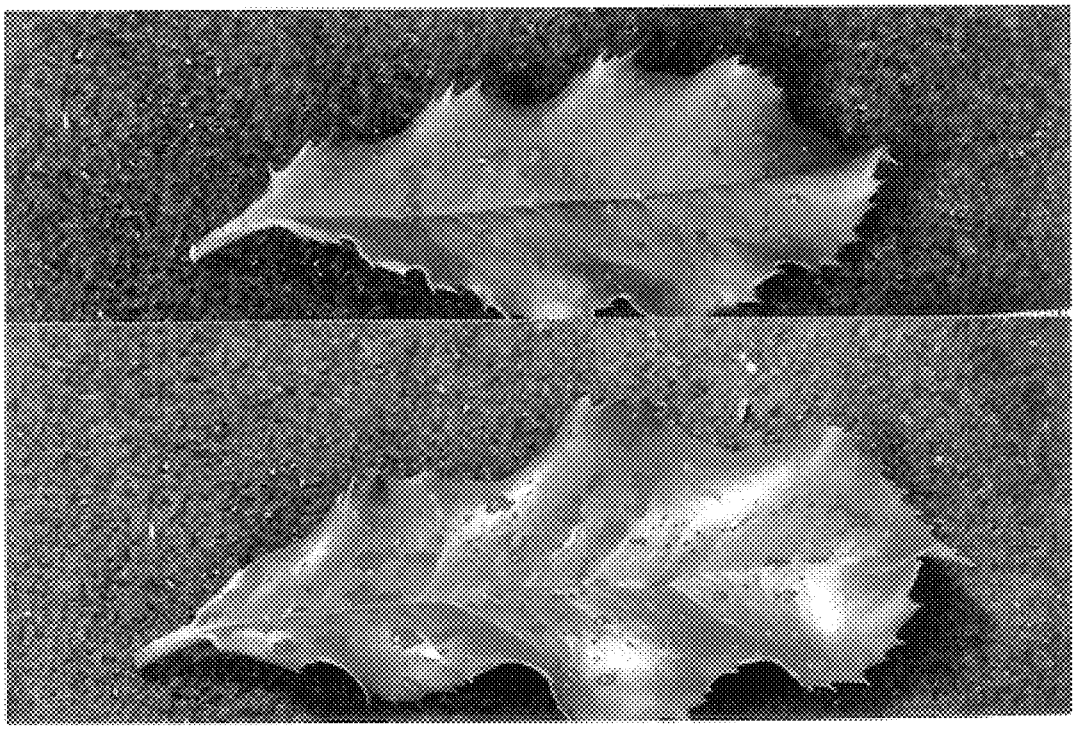

* * * * *